United States Patent [19]

Weinstein et al.

[11] Patent Number: 5,460,616
[45] Date of Patent: Oct. 24, 1995

[54] CATHETER INTRODUCER WITH FLUID CHAMBER VALVE

[75] Inventors: Lawrence A. Weinstein, Davie; Roberta D. Goode, Miami, both of Fla.

[73] Assignee: Cordis Corporation, Miami Lakes, Fla.

[21] Appl. No.: 230,335

[22] Filed: Apr. 19, 1994

[51] Int. Cl.$^6$ .................................................. A61M 5/00
[52] U.S. Cl. ........................ 604/167; 604/169; 604/256
[58] Field of Search .................................. 604/167, 256, 604/169

[56] References Cited

U.S. PATENT DOCUMENTS

| | | |
|---|---|---|
| 4,000,739 | 1/1977 | Stevens . |
| 4,240,411 | 12/1980 | Hosono ..................................... 604/167 |
| 4,421,296 | 12/1983 | Stephens . |
| 4,475,548 | 10/1984 | Muto ......................................... 604/167 |
| 4,626,245 | 12/1986 | Weinstein . |
| 4,813,938 | 3/1989 | Raulerson ................................ 604/167 |
| 4,895,346 | 1/1990 | Steigerwald ............................. 604/167 |
| 4,895,565 | 1/1990 | Hillstead . |
| 5,102,395 | 4/1992 | Cheer et al. ............................. 604/167 |
| 5,104,389 | 4/1992 | Deem et al. ............................. 604/167 |
| 5,176,652 | 1/1993 | Littrell ..................................... 604/167 |
| 5,189,607 | 2/1993 | Wu ........................................... 604/256 |
| 5,207,656 | 5/1993 | Kranys ..................................... 604/167 |
| 5,226,879 | 7/1993 | Ensminger et al. ..................... 604/167 |
| 5,279,571 | 1/1994 | Larkin ...................................... 604/167 |
| 5,389,080 | 2/1995 | Yoon ........................................ 604/167 |

Primary Examiner—Paul J. Hirsch
Attorney, Agent, or Firm—Gerstman, Ellis & McMillin, Ltd.

[57] ABSTRACT

A catheter introducer comprises a tubular sheath having an axis, and a housing carried on one end of the sheath. The housing encloses a fluid-filled chamber and carries a pair of valves aligned along the axis, the valves being at opposed ends of the fluid-filled chamber and communicating therewith. The valves serve to substantially retain the fluid within the housing, while allowing a catheter to pass through the valves and through the tubular sheath. The fluid of the chamber is preferably a gel or high viscosity liquid. The valves and fluid-filled chamber prevent the backflow of blood both in the presence and the absence of a catheter or the like extending through the valves and chamber.

15 Claims, 1 Drawing Sheet

CATHETER INTRODUCER WITH FLUID CHAMBER VALVE

BACKGROUND OF THE INVENTION

Catheter introducers are a well-known form of catheter, used to assist in the introduction of other catheters and guidewires to the arteriovenous system of a patient. Such catheter introducers comprise a tubular sheath or cannula having a housing carried on one end thereof, with the housing enclosing a hemostasis valve. Examples of such catheter introducers are numerous, with some being disclosed in Stevens U.S. Pat. Nos. 4,000,739 and 4,421,296. Other examples of catheter introducers are disclosed in Kranys U.S. Pat. No. 5,207,656; Weinstein U.S. Pat. No. 4,626,245; and Hillstead U.S. Pat. No. 4,895,565.

In the devices of the above described patents, the hemostasis valve comprises a flat, elastic partition seal with a center cut, either an aperture or a slit, through which a catheter (or guidewire) passes as it extends through the catheter introducer. These flat seals must be capable of allowing passage of catheters while maintaining sufficient elasticity to snap closed after removal thereof.

By this invention a valve is provided for a catheter introducer in which different valving principles are used to provide reliable hemostasis, so that blood at arterial pressure cannot flow out of the proximal end of the catheter introducer. Also, catheters passing through the valve of this invention are provided with lubrication for improved reduction in friction as the catheter is advanced through the entire catheter introducer and into the arteriovenous system of a patient.

DESCRIPTION OF THE INVENTION

By this invention a catheter introducer is provided which comprises a tubular sheath, (which may be similar to conventional catheter introducers) and which carries a housing on one end of the sheath. The housing encloses a fluid-filled chamber, and carries a pair of valves which are aligned along the axis of the tubular sheath. The valves serve to substantially retain the fluid within the housing, while allowing a catheter (or guidewire) to pass through the valves and through the tubular sheath. The valves and the fluid-filled chamber prevent the backflow of blood out of the proximal end of the catheter introducer, both in the presence and in the absence of a catheter extending therethrough.

Preferably, the fluid present in the fluid-filled chamber is a gel, for example, a silicone gel or petroleum jelly. The gels or other fluids used herein are preferably hydrophobic in nature so that they are not miscible with blood. Alternatively, the fluid may be a viscous fluid which is not gelled, having a viscosity of typically at least about ten thousand centistokes (cs.), up to a million or more centistokes, as may be desired. Specifically, silicone fluids such as dimethylpolysiloxane may be used.

The valves which are aligned along the sheath axis communicate with the fluid-filled chamber to permit a catheter or a guidewire to pass entirely through the fluid-filled chamber, and to continue on through the housing and the tubular sheath of the catheter introducer. The valves may be made of a slit, flexible membrane, for example flexible membranes with a tricuspid-forming slit as disclosed, for example, in Hillstead U.S. Pat. No. 4,895,565. Alternatively, duckbill valves or other desired valves may be used to provide sealing passage of an elongated member such as a catheter, while substantially retaining the fluid in the fluid-filled chamber.

The housing may carry an inner container, if desired, which holds the fluid and carries the valves described above. This inner container may be spheroidal in shape, particularly being substantially ovoid with the respective valves being at opposite ends of the ovoid inner container along the major axis thereof. Alternatively the housing itself may serve as the container, and may carry the valves and enclose the fluid-filled chamber without any inner wall member.

Thus, when a catheter passes through the housing of a catheter introducer in accordance with this invention, to extend through the sheath into the arteriovenous system of a patient, it passes through the pair of valves aligned along the sheath axis, and also the typically-gelled fluid within the chamber. The catheter receives lubrication from the gel or other fluid in the chamber as it advances. Also, the arrangement as described provides very substantial protection against back leakage of blood, due to the presence of the fluid, which provides added resistance to the back bleeding of blood out of the proximal end of the catheter introducer, even through the blood in the sheath may be at arterial pressure.

A separate, inner container which can hold the fluid and carry the valves may be separately inserted into the housing if desired when a special need for sealing is identified during the middle of an operation, replacing another valve. Also, the respective inner containers may be switched, if desired, with one inner container carrying a fluid of differing and better characteristics for the particular purpose, for example a gel of greater molecular weight and stiffness than the fluid of a prior inner container which has been replaced. Thus, effective hemostasis, coupled with a low degree of friction during catheter advancement, may be provided by this invention.

DESCRIPTION OF SPECIFIC EMBODIMENTS

Figure 1:
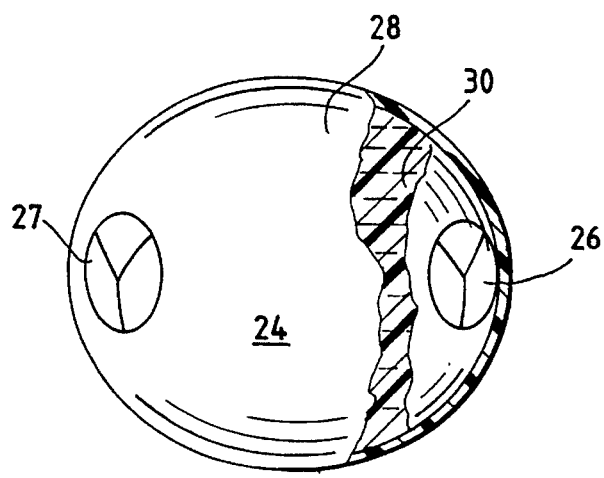
FIG. 1 shows a spheroidal inner container which may be placed in the housing of a catheter introducer, with some parts of the inner container removed for clarity.
Figure 2:
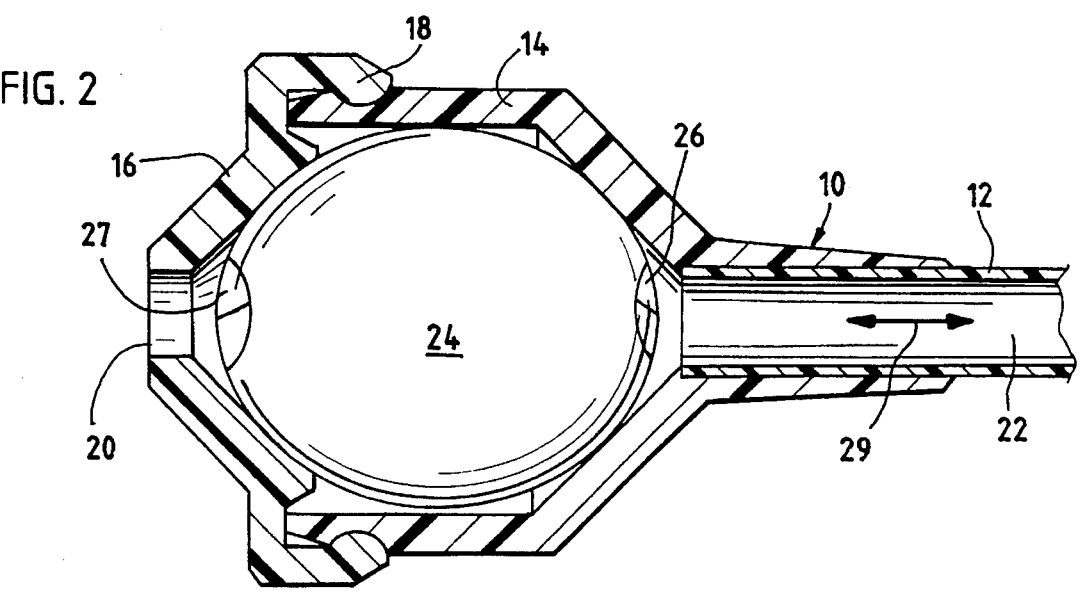
FIG. 2 is a longitudinal, fragmentary, sectional view of a catheter introducer in which the housing contains the inner container of FIG. 1.

Referring to the drawings, the proximal section of a catheter introducer 10 is shown. Introducer 10 is similar to those of the prior art except as otherwise shown herein. A conventional sheath 12 carries a housing 14 on its distal end. Housing 14 is closed with a cap 16 which may snap fit into place, having a snap-fit flange 18 as shown. Cap 16 may otherwise be permanently sealed in position.

Cap 16 defines an aperture 20 for access by a catheter or guidewire into the catheter sheath introducer, after the sheath introducer has been emplaced in the arterial system of a patient.

As is conventional, catheter sheath introducer 10 is emplaced in an artery of the patient for angiography or angioplasty, as needed. This is conventionally accomplished by placing a conventional dilator stylette through the bore 22 of sheath 12, with the stylette also extending through aperture 20 and the spheroidal valve member 24. Tricuspid valves 26, 27 are provided, being aligned along the axis 29 of sheath 12 and spaced at opposite ends of spheroidal inner container 28, which specifically is oval in shape as shown. Inner container 28 is filled with a silicone or petroleum jelly 30.

Figure 3:
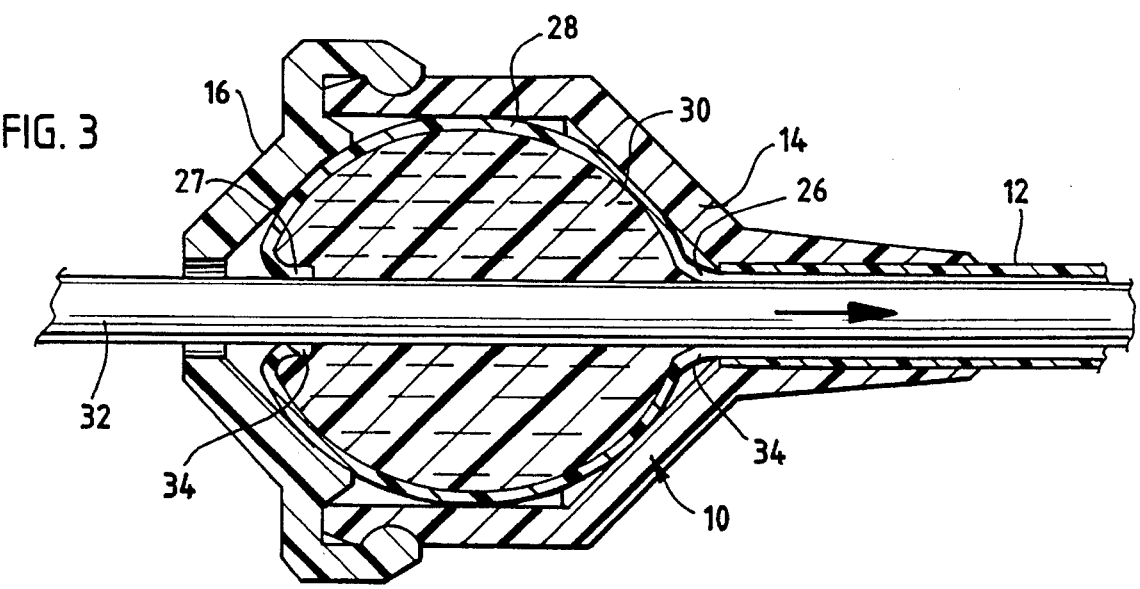
FIG. 3 is a longitudinal, fragmentary, sectional view of the catheter introducer of FIG. 2, with the inner container being shown in section as well, and also showing a catheter being advanced therethrough.

Thus, a conventional dilator stylette is passed through the aperture 20, valves 26, 27, and sheath 12, in a manner similar to that illustrated in FIG. 3. to conventionally permit the emplacement of catheter sheath introducer 10 into a patient's arterial system. Then, as the dilator is removed, bore 22 of sheath 12 is exposed to blood at arterial pressure, causing a backflow of blood through sheath 12 to the spheroidal valve member 24. There, the backflow of blood is stopped by the valving action, since the blood cannot effectively pass through the tricuspid valve 26 to displace the gel 30 from inner container 28. Likewise, the blood cannot effectively mix with the gel 30, because of the preferred strong hydrophobic characteristic of the gel. Thus effective sealing is provided.

FIG. 3 shows catheter introducer 10 with a catheter 32 extending therethrough, into the arterial system of a patient. The deflected leaves 34 of the tricuspid valves 26, 27 are shown, which fold around the catheter 32 (and the dilator stylette before the catheter) to provide sealing. However, because of the presence of the preferred gel 30, the sealing is markedly improved over a simple tricuspid seal without the gel, since the blood cannot substantially displace the gel, and thus is prevented from flowing through inner container 28. Seals may be provided between inner container 24 and housing 14 to prevent blood migration between them.

Also, the presence of gel 30 provides a lubricating coating to catheter 32 and any other elongated member that passes through catheter introducer 10, to facilitate the lubricity and easy advancement thereof. The tricuspid valves 26, 27 may be made of a relatively soft rubber with less concern about high performance sealing characteristics, since the gel 30 is present to provide the necessary sealing.

With typical tricuspid valves which may, if desired, be formed from an elastomeric membrane with a simple Y-shaped cut, there is little leakage of gel 30 out of the valves because of the high viscosity of the gel.

Thus, a catheter introducer is provided in which a catheter may be advanced therethrough with low friction, while at the same time a high degree of sealing against backbleeding is provided.

The above has been offered for illustrative purposes only, and is not intended to limit the scope of the invention of this application, which is as defined in the claims below.

That which is claimed is:

1. A catheter introducer which comprises a tubular sheath having an axis, and a housing carried on one end of said sheath, said housing enclosing a fluid-filled chamber large enough to permit said catheter to extend through said chamber, said chamber carrying a pair of valves aligned along said axis and communicating with said fluid-filled chamber, said valves serving to substantially retain said fluid within said housing while allowing a catheter to pass through said valves and through said tubular sheath, whereby said valves and fluid-filled chamber prevent the backflow of blood both in the presence and the absence of a catheter extending through said valves.

2. The catheter introducer of claim 1 in which said fluid is a hydrophobic gel.

3. The catheter introducer of claim 1 in which said fluid is a silicone having a viscosity of at least about 10,000 cs.

4. The catheter introducer of claim 1 in which said housing carries an inner container which holds said fluid and carries said valves.

5. The catheter introducer of claim 4 in which said inner container is spheroidal in shape.

6. The catheter introducer of claim 1 in which said valves are tricuspid valves.

7. A catheter introducer which comprises a tubular sheath having an axis, and a housing carried on one end of said sheath, said housing enclosing a fluid-filled chamber large enough to permit said catheter to extend through said chamber, said chamber carrying a pair of tricuspid valves aligned along said axis on opposed ends of the fluid-filled chamber and communicating with said fluid-filled chamber, said valves serving to substantially retain said fluid within said housing while allowing a catheter to pass through said tricuspid valves and through said tubular sheath, said fluid of the fluid-filled chamber being a hydrophobic gel, whereby said valves and fluid-filled chamber prevent the backflow of blood both in the presence and in the absence of a catheter extending through said valves.

8. The catheter introducer of claim 7 in which said housing carries an inner container which, in turn, carries, said gel and valves.

9. The catheter introducer of claim 8 in which said inner container is spheroidal in shape.

10. The catheter introducer of claim 7 in which said gel is a petroleum gel.

11. A catheter introducer which comprises a tubular sheath having an axis, and a housing carried on one end of said sheath, said housing enclosing a fluid-filled chamber large enough to permit said catheter to extend through said chamber, said chamber carrying a pair of valves aligned along said axis on opposed ends of said fluid-filled chamber, said valves communicating with said fluid-filled chamber, said valves serving to substantially retain said fluid within the housing while allowing a catheter to pass through said valves and through said tubular sheath, said fluid comprising a hydrophobic fluid, whereby said valves and fluid-filled chamber prevent the backflow of blood both in the presence and the absence of a catheter extending through said valves.

12. The catheter introducer of claim 11 in which said housing carries an inner container which holds said fluid and carries said valves.

13. The catheter introducer of claim 12 in which said inner container is spheroidal in shape, said valves being essentially positioned at the respective ends of the major axis of said spheroidal shape.

14. The catheter introducer of claim 13 in which said valves are tricuspid valves.

15. The catheter introducer of claim 14 in which said gel is a petroleum gel.

* * * * *